(12) United States Patent
Gonzalez-Hernandez

(10) Patent No.: US 9,402,667 B2
(45) Date of Patent: Aug. 2, 2016

(54) APPARATUS AND METHOD FOR USE OF THE APPARATUS FOR FRACTURE FIXATION OF THE DISTAL HUMERUS

(71) Applicant: Eduardo Gonzalez-Hernandez, Coconut Grove, FL (US)

(72) Inventor: Eduardo Gonzalez-Hernandez, Coconut Grove, FL (US)

( * ) Notice: Subject to any disclaimer, the term of this patent is extended or adjusted under 35 U.S.C. 154(b) by 598 days.

(21) Appl. No.: 13/673,861

(22) Filed: Nov. 9, 2012

(65) Prior Publication Data
US 2013/0116734 A1 May 9, 2013

Related U.S. Application Data

(60) Provisional application No. 61/557,647, filed on Nov. 9, 2011.

(51) Int. Cl.
*A61B 17/80* (2006.01)
*A61B 17/86* (2006.01)

(52) U.S. Cl.
CPC ........... *A61B 17/8061* (2013.01); *A61B 17/864* (2013.01); *A61B 17/8625* (2013.01)

(58) Field of Classification Search
CPC ............... A61B 17/80; A61B 17/8061; A61B 17/8625; A61B 17/864; A61B 17/8033; A61B 17/72; A61B 17/7208; A61B 17/7216; A61B 17/7225
USPC ................................ 606/64, 70–71, 280–321
See application file for complete search history.

(56) References Cited

U.S. PATENT DOCUMENTS

| | | | |
|---|---|---|---|
| 1,950,799 A | 3/1934 | Jones | |
| 2,500,370 A | 3/1950 | McKibbin | |
| 2,555,291 A | 5/1951 | Poupitch | |
| 2,682,265 A | 6/1954 | Collison | |
| 2,853,114 A | 9/1958 | Barry | |
| 2,875,663 A | 3/1959 | Wieber | |
| 3,489,143 A | 1/1970 | Halloran | |
| 3,552,389 A | 1/1971 | Allgower et al. | |
| 3,579,831 A | 5/1971 | Stevens et al. | |
| 3,716,050 A | 2/1973 | Johnston | |

(Continued)

FOREIGN PATENT DOCUMENTS

| DE | 86 28 766 U1 | 12/1986 |
|---|---|---|
| DE | 89 07 443 U1 | 9/1989 |

(Continued)

OTHER PUBLICATIONS

U.S. Appl. No. 13/663,129, filed Oct. 2012, Gonzalez-Hernandez.

(Continued)

*Primary Examiner* — Anu Ramana
*Assistant Examiner* — Jessica Weiss
(74) *Attorney, Agent, or Firm* — Martin & Ferraro, LLP

(57) ABSTRACT

A system for fixing fractured bone portions of a distal humerus in position with respect to one another. In one embodiment, the system includes a plate portion, a projection portion, and a fixation post. The plate portion includes a surface for contacting a posterior portion of the distal humerus adjacent one of a lateral side and a medial side thereof. The projection portion extends outwardly from the plate portion and includes an aperture for receiving the fixation post. The fixation post includes at least one fenestration, and extends from adjacent the one of the lateral and medial sides of the distal humerus to adjacent the other of the lateral and medial sides of the distal humerus.

9 Claims, 6 Drawing Sheets

(56) References Cited

U.S. PATENT DOCUMENTS

| | | | |
|---|---|---|---|
| 3,791,380 A | 2/1974 | Dawidowski |
| 3,824,995 A | 7/1974 | Getscher |
| 3,900,025 A | 8/1975 | Barnes, Jr. |
| 4,263,904 A | 4/1981 | Judet |
| 4,535,768 A | 8/1985 | Hourahane et al. |
| 4,683,878 A | 8/1987 | Carter |
| 4,733,654 A | 3/1988 | Marino |
| 4,776,330 A | 10/1988 | Chapman et al. |
| 4,790,302 A | 12/1988 | Colwill et al. |
| 4,794,919 A | 1/1989 | Nilsson |
| 4,796,612 A | 1/1989 | Reese |
| 4,838,264 A | 6/1989 | Bremer et al. |
| 4,858,602 A | 8/1989 | Seidel et al. |
| 4,870,957 A | 10/1989 | Goble et al. |
| 5,003,969 A | 4/1991 | Azer et al. |
| 5,015,248 A | 5/1991 | Burstein et al. |
| 5,041,113 A | 8/1991 | Biedermann et al. |
| 5,041,114 A | 8/1991 | Chapman et al. |
| 5,180,383 A | 1/1993 | Haydon |
| 5,190,544 A | 3/1993 | Chapman et al. |
| 5,324,291 A | 6/1994 | Ries et al. |
| 5,356,410 A | 10/1994 | Pennig |
| 5,364,399 A | 11/1994 | Lowery et al. |
| 5,423,860 A | 6/1995 | Lizardi et al. |
| 5,437,667 A | 8/1995 | Papierski et al. |
| 5,443,516 A | 8/1995 | Albrektsson et al. |
| 5,458,654 A | 10/1995 | Tepic |
| 5,462,547 A | 10/1995 | Weigum |
| 5,472,444 A | 12/1995 | Huebner et al. |
| 5,505,734 A | 4/1996 | Caniggia et al. |
| 5,578,035 A | 11/1996 | Lin |
| 5,584,835 A | 12/1996 | Greenfield |
| 5,586,985 A | 12/1996 | Putnam et al. |
| 5,601,553 A | 2/1997 | Trebing et al. |
| 5,620,449 A | 4/1997 | Faccioli et al. |
| 5,658,287 A | 8/1997 | Hofmann et al. |
| 5,665,088 A | 9/1997 | Gil et al. |
| 5,674,222 A | 10/1997 | Berger et al. |
| 5,676,667 A | 10/1997 | Hausman |
| 5,681,311 A | 10/1997 | Foley et al. |
| 5,709,686 A | 1/1998 | Talos et al. |
| 5,749,872 A | 5/1998 | Kyle et al. |
| 5,766,174 A | 6/1998 | Perry |
| 5,776,194 A | 7/1998 | Mikol et al. |
| 5,779,704 A | 7/1998 | Kim |
| 5,785,712 A | 7/1998 | Runciman et al. |
| 5,840,078 A | 11/1998 | Yerys |
| 5,868,749 A | 2/1999 | Reed |
| 5,931,839 A | 8/1999 | Medoff |
| 5,976,139 A | 11/1999 | Bramlet |
| 5,980,575 A | 11/1999 | Albrektsson et al. |
| 6,030,389 A | 2/2000 | Wagner et al. |
| 6,096,040 A | 8/2000 | Esser |
| 6,149,653 A | 11/2000 | Deslauriers |
| 6,152,927 A | 11/2000 | Farris et al. |
| 6,200,330 B1 | 3/2001 | Benderev et al. |
| 6,206,881 B1 | 3/2001 | Frigg et al. |
| D443,060 S | 5/2001 | Benirschke et al. |
| 6,270,499 B1 | 8/2001 | Leu et al. |
| D449,692 S | 10/2001 | Michelson |
| 6,302,887 B1 | 10/2001 | Spranza et al. |
| 6,331,179 B1 | 12/2001 | Freid et al. |
| 6,348,052 B1 | 2/2002 | Sammarco |
| 6,358,250 B1 | 3/2002 | Orbay |
| 6,364,881 B1 | 4/2002 | Apgar et al. |
| 6,364,882 B1 | 4/2002 | Orbay |
| 6,379,359 B1 | 4/2002 | Dahners |
| 6,398,783 B1 | 6/2002 | Michelson |
| 6,406,478 B1 | 6/2002 | Kuo |
| 6,409,768 B1 | 6/2002 | Tepic et al. |
| 6,413,259 B1 | 7/2002 | Lyons et al. |
| 6,440,135 B2 | 8/2002 | Orbay et al. |
| 6,468,278 B1 | 10/2002 | Muckter |
| 6,572,620 B1 | 6/2003 | Schon et al. |
| 6,620,195 B2 | 9/2003 | Goble et al. |
| 6,623,486 B1 | 9/2003 | Weaver et al. |
| 6,663,669 B1 | 12/2003 | Reiley |
| 6,669,701 B2 | 12/2003 | Steiner et al. |
| 6,695,844 B2 | 2/2004 | Bramlet et al. |
| 6,706,046 B2 | 3/2004 | Orbay et al. |
| 6,712,820 B2 | 3/2004 | Orbay |
| 6,719,759 B2 | 4/2004 | Wagner et al. |
| 6,730,090 B2 | 5/2004 | Orbay et al. |
| 6,776,781 B1 | 8/2004 | Uwaydah |
| 6,863,671 B1 | 3/2005 | Strobel et al. |
| 6,866,665 B2 | 3/2005 | Orbay |
| 6,916,323 B2 | 7/2005 | Kitchens |
| 6,945,973 B2 | 9/2005 | Bray |
| 7,001,388 B2 | 2/2006 | Orbay et al. |
| 7,063,701 B2 | 6/2006 | Michelson |
| 7,128,744 B2 | 10/2006 | Weaver et al. |
| D536,453 S | 2/2007 | Young et al. |
| 7,220,246 B2 | 5/2007 | Raulerson |
| 7,229,444 B2 | 6/2007 | Boyd |
| 7,229,445 B2 | 6/2007 | Hayeck et al. |
| 7,235,079 B2 | 6/2007 | Jensen et al. |
| 7,354,441 B2 | 4/2008 | Frigg |
| 7,500,983 B1 | 3/2009 | Kaiser et al. |
| 7,563,263 B2 | 7/2009 | Orbay et al. |
| 7,582,107 B2 | 9/2009 | Trail et al. |
| 7,591,823 B2 | 9/2009 | Tipirneni |
| 7,604,657 B2 | 10/2009 | Orbay et al. |
| 7,637,908 B1 | 12/2009 | Gonzalez-Hernandez |
| 7,651,517 B2 | 1/2010 | Konieczynski et al. |
| 7,655,029 B2 | 2/2010 | Niederberger et al. |
| 7,695,472 B2 | 4/2010 | Young |
| 7,722,653 B2 | 5/2010 | Young et al. |
| 7,740,648 B2 | 6/2010 | Young et al. |
| 7,744,638 B2 | 6/2010 | Orbay |
| 7,776,076 B2 | 8/2010 | Grady, Jr. et al. |
| 7,780,667 B2 | 8/2010 | Watanabe et al. |
| 7,780,710 B2 | 8/2010 | Orbay et al. |
| 7,896,886 B2 | 3/2011 | Orbay et al. |
| 7,909,859 B2 | 3/2011 | Mosca et al. |
| 7,914,532 B2 | 3/2011 | Shaver et al. |
| 7,927,341 B2 | 4/2011 | Orbay et al. |
| 7,938,850 B2 | 5/2011 | Orbay et al. |
| 7,951,176 B2 | 5/2011 | Grady et al. |
| 7,951,178 B2 | 5/2011 | Jensen |
| 7,955,364 B2 | 6/2011 | Ziolo et al. |
| D643,121 S | 8/2011 | Milford et al. |
| 8,021,402 B2 | 9/2011 | Martin et al. |
| D646,785 S | 10/2011 | Milford |
| 8,062,296 B2 | 11/2011 | Orbay et al. |
| 8,062,367 B2 | 11/2011 | Kirschman |
| 8,100,953 B2 | 1/2012 | White et al. |
| 8,182,485 B1 | 5/2012 | Gonzalez-Hernandez |
| 8,317,842 B2 | 11/2012 | Graham et al. |
| 8,523,902 B2 | 9/2013 | Heaven et al. |
| 8,574,234 B2 | 11/2013 | Gonzalez-Hernandez |
| 8,597,363 B2 | 12/2013 | Liverneaux et al. |
| 8,728,126 B2 | 5/2014 | Steffen |
| 8,764,808 B2 | 7/2014 | Gonzalez-Hernandez |
| 8,906,070 B2 | 12/2014 | Medoff |
| 2002/0091391 A1 | 7/2002 | Cole et al. |
| 2003/0135212 A1 | 7/2003 | Chow |
| 2003/0135216 A1 | 7/2003 | Sevrain |
| 2003/0208210 A1 | 11/2003 | Dreyfuss et al. |
| 2004/0097939 A1 | 5/2004 | Bonutti |
| 2004/0193278 A1 | 9/2004 | Maroney et al. |
| 2004/0199258 A1 | 10/2004 | Macara |
| 2004/0210220 A1 | 10/2004 | Tornier |
| 2005/0004574 A1 | 1/2005 | Muckter |
| 2005/0015089 A1 | 1/2005 | Young et al. |
| 2005/0021033 A1 | 1/2005 | Zeiler et al. |
| 2005/0038513 A1 | 2/2005 | Michelson |
| 2005/0085819 A1 | 4/2005 | Ellis et al. |
| 2005/0182405 A1* | 8/2005 | Orbay et al. ............ 606/69 |
| 2005/0240187 A1 | 10/2005 | Huebner et al. |
| 2005/0267476 A1 | 12/2005 | Chervitz et al. |
| 2005/0288681 A1 | 12/2005 | Klotz et al. |
| 2006/0015072 A1 | 1/2006 | Raulerson |
| 2006/0015101 A1 | 1/2006 | Warburton et al. |
| 2006/0058795 A1 | 3/2006 | Boyd |

(56) References Cited

U.S. PATENT DOCUMENTS

| | | |
|---|---|---|
| 2006/0106385 A1* | 5/2006 | Pennig .................... 606/64 |
| 2006/0161156 A1 | 7/2006 | Orbay |
| 2006/0217722 A1 | 9/2006 | Dutoit et al. |
| 2006/0229623 A1 | 10/2006 | Bonutti et al. |
| 2006/0235400 A1 | 10/2006 | Schneider |
| 2006/0241617 A1 | 10/2006 | Holloway et al. |
| 2006/0264947 A1 | 11/2006 | Orbay et al. |
| 2006/0264956 A1 | 11/2006 | Orbay et al. |
| 2006/0271105 A1 | 11/2006 | Foerster et al. |
| 2007/0005074 A1 | 1/2007 | Chudik |
| 2007/0016205 A1 | 1/2007 | Buetter et al. |
| 2007/0083207 A1 | 4/2007 | Ziolo et al. |
| 2007/0123880 A1 | 5/2007 | Medoff |
| 2007/0123885 A1 | 5/2007 | Kirschman |
| 2007/0162015 A1 | 7/2007 | Winquist et al. |
| 2007/0167953 A1 | 7/2007 | Prien et al. |
| 2007/0233113 A1 | 10/2007 | Kaelblein |
| 2007/0233114 A1 | 10/2007 | Bouman |
| 2007/0233115 A1 | 10/2007 | Sixto et al. |
| 2007/0265631 A1 | 11/2007 | Fox |
| 2008/0015593 A1 | 1/2008 | Pfefferle et al. |
| 2008/0045960 A1 | 2/2008 | Bruecker et al. |
| 2008/0119895 A1 | 5/2008 | Manceau |
| 2008/0132955 A1 | 6/2008 | Frigg |
| 2008/0140130 A1 | 6/2008 | Chan et al. |
| 2008/0154311 A1 | 6/2008 | Staeubli |
| 2008/0161853 A1 | 7/2008 | Arnold et al. |
| 2008/0161860 A1 | 7/2008 | Ahrens et al. |
| 2008/0161863 A1 | 7/2008 | Arnold et al. |
| 2008/0221577 A1 | 9/2008 | Elghazaly |
| 2008/0234749 A1 | 9/2008 | Forstein |
| 2008/0234752 A1 | 9/2008 | Dahners |
| 2008/0249572 A1 | 10/2008 | Tandon |
| 2009/0012571 A1 | 1/2009 | Perrow et al. |
| 2009/0024173 A1 | 1/2009 | Reis, Jr. |
| 2009/0048681 A1 | 2/2009 | Vlachos |
| 2009/0069851 A1 | 3/2009 | Gillard |
| 2009/0076554 A1 | 3/2009 | Huebner et al. |
| 2009/0105838 A1 | 4/2009 | Russo et al. |
| 2009/0118769 A1 | 5/2009 | Sixto, Jr. |
| 2009/0125070 A1 | 5/2009 | Sixto, Jr. et al. |
| 2009/0171399 A1 | 7/2009 | White et al. |
| 2009/0192550 A1 | 7/2009 | Leung et al. |
| 2009/0216270 A1 | 8/2009 | Humphrey |
| 2009/0228010 A1 | 9/2009 | Gonzalez-Hernandez et al. |
| 2009/0254089 A1 | 10/2009 | Tipirneni et al. |
| 2009/0254189 A1 | 10/2009 | Scheker |
| 2009/0264936 A1 | 10/2009 | Gonzalez-Hernandez |
| 2009/0275987 A1 | 11/2009 | Graham et al. |
| 2009/0275991 A1 | 11/2009 | Medoff |
| 2009/0281577 A1 | 11/2009 | Graham et al. |
| 2009/0281578 A1 | 11/2009 | Spencer |
| 2009/0299369 A1 | 12/2009 | Orbay et al. |
| 2009/0306711 A1 | 12/2009 | Stone et al. |
| 2009/0312758 A1 | 12/2009 | Petit |
| 2009/0312760 A1 | 12/2009 | Forstein et al. |
| 2009/0312802 A1 | 12/2009 | Dasilva |
| 2009/0326591 A1 | 12/2009 | Spencer, Jr. |
| 2010/0030276 A1 | 2/2010 | Huebner et al. |
| 2010/0057086 A1 | 3/2010 | Price et al. |
| 2010/0094358 A1 | 4/2010 | Moore |
| 2010/0145339 A1 | 6/2010 | Steffen |
| 2010/0145397 A1* | 6/2010 | Overes et al. ............. 606/319 |
| 2010/0198258 A1 | 8/2010 | Heaven et al. |
| 2010/0217393 A1 | 8/2010 | Theofilos |
| 2010/0262194 A1 | 10/2010 | Wagner |
| 2010/0274245 A1 | 10/2010 | Gonzalez-Hernandez |
| 2010/0324602 A1 | 12/2010 | Huebner et al. |
| 2010/0331844 A1 | 12/2010 | Ellis et al. |
| 2011/0152943 A1 | 6/2011 | Gonzalez-Hernandez |
| 2011/0160730 A1 | 6/2011 | Schonhardt et al. |
| 2012/0083848 A1 | 4/2012 | Gonzalez-Hernandez |
| 2012/0109322 A1 | 5/2012 | Gonzalez-Hernandez |
| 2012/0197305 A1 | 8/2012 | Gonzalez-Hernandez |
| 2012/0197308 A1 | 8/2012 | Gonzalez-Hernandez |
| 2012/0226321 A1 | 9/2012 | Gonzalez-Hernandez |
| 2012/0226322 A1 | 9/2012 | Gonzalez-Hernandez |
| 2012/0226323 A1 | 9/2012 | Gonzalez-Hernandez |
| 2013/0096629 A1 | 4/2013 | Rollinghoff et al. |
| 2013/0289627 A1 | 10/2013 | Gonzalez-Hernandez |
| 2013/0338780 A1 | 12/2013 | Berchoux et al. |
| 2014/0121709 A1 | 5/2014 | Gonzalez-Hernandez |
| 2014/0121779 A1 | 5/2014 | Gonzalez-Hernandez |
| 2014/0172020 A1 | 6/2014 | Gonzalez-Hernandez |
| 2014/0180344 A1 | 6/2014 | Gonzalez-Hernandez |
| 2014/0277177 A1 | 9/2014 | Gonzalez-Hernandez |
| 2015/0045898 A1 | 2/2015 | Gonzalez-Hernandez |
| 2015/0164566 A1 | 6/2015 | Gonzalez-Hernandez |

FOREIGN PATENT DOCUMENTS

| | | |
|---|---|---|
| DE | 43 43 117 A1 | 6/1995 |
| DE | 198 57 279 A1 | 6/2000 |
| DE | 299 07 161 U1 | 8/2000 |
| EP | 0 551 588 A1 | 11/1992 |
| EP | 1 132 052 A2 | 9/2001 |
| EP | 1 468 655 A2 | 10/2004 |
| FR | 2 606 268 A1 | 5/1988 |
| FR | 2 680 673 A1 | 3/1993 |
| FR | 2 712 173 A1 | 5/1995 |
| JP | 4-138152 A | 5/1992 |
| WO | WO 99/38448 A1 | 8/1999 |
| WO | WO 02/071963 A1 | 9/2002 |
| WO | WO 2005/037117 A1 | 4/2005 |
| WO | WO 2008/007194 A2 | 1/2008 |
| WO | WO 2008/007196 A2 | 1/2008 |
| WO | WO 2012/003884 | 1/2012 |

OTHER PUBLICATIONS

U.S. Appl. No. 13/663,209, filed Oct. 2012, Gonzalez-Hernandez.
U.S. Appl. No. 13/840,194, filed Mar. 2013, Gonzalez-Hernandez.
U.S. Appl. No. 14/189,681, filed Feb. 2014, Gonzalez-Hernandez.
U.S. Appl. No. 14/213,310, filed Mar. 2014, Gonzalez-Hernandez.
U.S. Appl. No. 10/993,723, filed Nov. 2004, Gonzalez-Hernandez.
U.S. Appl. No. 11/079,350, filed Mar. 2005, Gonzalez-Hernandez.
U.S. Appl. No. 11/366,676, filed Mar. 2006, Gonzalez-Hernandez.
U.S. Appl. No. 11/493,122, filed Jul. 2006, Gonzalez-Hernandez.
U.S. Appl. No. 11/526,331, filed Sep. 2006, Gonzalez-Hernandez.
U.S. Appl. No. 11/707,775, filed Feb. 2007, Gonzalez-Hernandez.
Acumed; ACU-LOC Wrist Plating System; Jul. 2009; 20 pages.
Acumed; The Mayo Clinic Congruent Elbow Plates (catalog); 2003; 19 pages.
Acumed; The Mayo Clinic Congruent Elbow Plate System (catalog); Apr. 2006; 20 pages.
Christie, J., C.R. Howie and P.C. Armour, Fixation of displaced subcapital femoral fractures. Compression screw fixation versus double divergent pins. *J Bone Joint Surg [Br]* 1988; 70-B: 199-201.
Cross, W.M. et al., "Achieving stable fixation: biomechanical designs for fracture healing," AAOS Now (2008) 3 pages.
Guha, AR, et al.; "A new Technique of Fixation of Radial Head Fractures Using a modified Tubular Plate, " Journal of Postgraduate Medicine; Jul. 2004; vol. 50, Issue 2; pp. 113-114; Accessed Aug. 6, 2008 at: http://www.jpgmonline.com/article.asp?issn=0022-3859; year=2004;volume=50;issue=2;spage=113;epage=114;aulast= Guha.
Hand Innovations, LLC; DVR Anatomic, Volar Plating System; 2007; 4 pages.
Hussain M., R.N. Natarajan, A.H. Fayyazi, B.R. Braaksma, G.B. Andersson and H.S. An, *Screw angulation affects bone-screw stresses and bone graft load sharing in an anterior cervical corpectomy fusion with a rigid screw-plate construct: a finite element model study*; Spine Journal, vol. 9, Issue 12; Dec. 2009; pp. 1016-1023 (published online Oct. 12, 2009).
Lakatos, R. et al.; "General principles of internal fixation"; eMedicine; Aug. 2006; 51 pages.
"MIS Technique," published by Zimmer®, 1 page, prior to Nov. 19, 2004.
Postak, Paul D.; "Biomechanical Properties of Fixed-Angle Volar Distal Radius Plates Under Dynamic loading;" 2007; 6 pages.

(56) References Cited

OTHER PUBLICATIONS

Robert, III, K.Q., R. Changler, R.V. Barratta, K.A. Thomas and M.B. Harris, The effect of divergent screw placement on the initial strength of plate-to-bone fixation. *J Trauma*. Dec. 2003;55(6):1139-44.

Synthes, "Large Fragment LCP Instrument and Implant Set;" technique guide; 2003; 31 pages.

Synthes; 3.5 mm LCP Periarticular Proximal Humerus Plate; Apr. 2010; 22 pages.

Synthes; Locking Compression Plate (LCP) System (brochure); 2003; 6 pages.

Synthes, "Locking Compression Plate (LCP) System. Locking screw technology and conventional plating in one system;" 2003; 6 pages.

Synthes; Locking Compression Plate (LCP) System (brochure); Jan. 2007; 6 pages.

Synthes; Modular Mini Fragment LCP System (brochure); 2007; 12 pages.

Synthes; Small Fragment Locking Compression Plate (LCP) System (brochure); 2002; 43 pages.

Written Opinion of the International Searching Authority; International Application No. PCT/US2009/036211; Sep. 23, 2010; 8 pages.

"Zimmer® Universal Locking System," The Journal of Bone and Joint Surgery, vol. 89, No. 7, Jul. 2007, 1 page.

Zimmer, Inc. "Zimmer® Universal Locking System," brochure (2006), 4 pages.

Zimmer, Inc.; "Zimmer Universal Locking System;" brochure; 2009, 2 pages.

Zimmer, Inc. "Zimmer Holdings to Launch Innovative Locking Plate System at Orthopaedic Trauma Association Meeting," Sep. 14, 2006; 3 pages.

Zimmer, Inc.; "Zimmer Small Fragment Universal Locking System;" Surgical Technique; 2010; 16 pages.

Zimmer; Zimmer Periarticular Plating System-Low-Profile Fixation (catalog); 2003; 8 pages.

\* cited by examiner

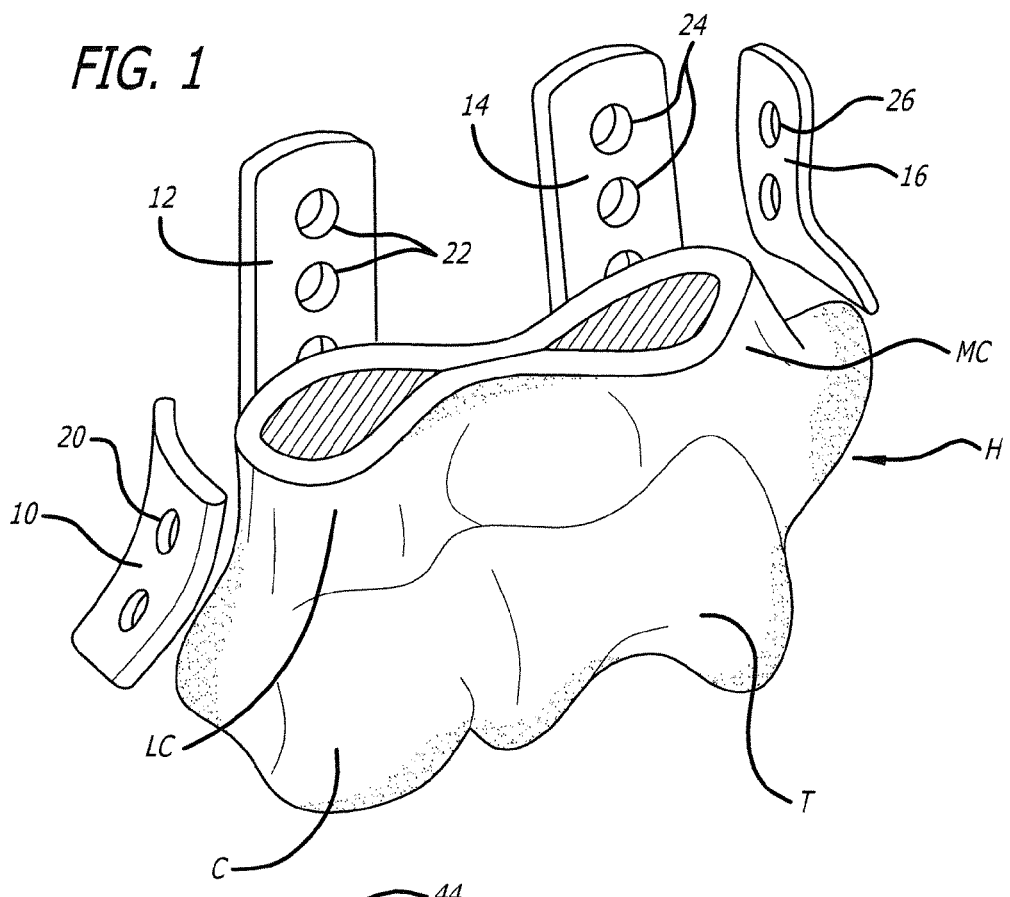
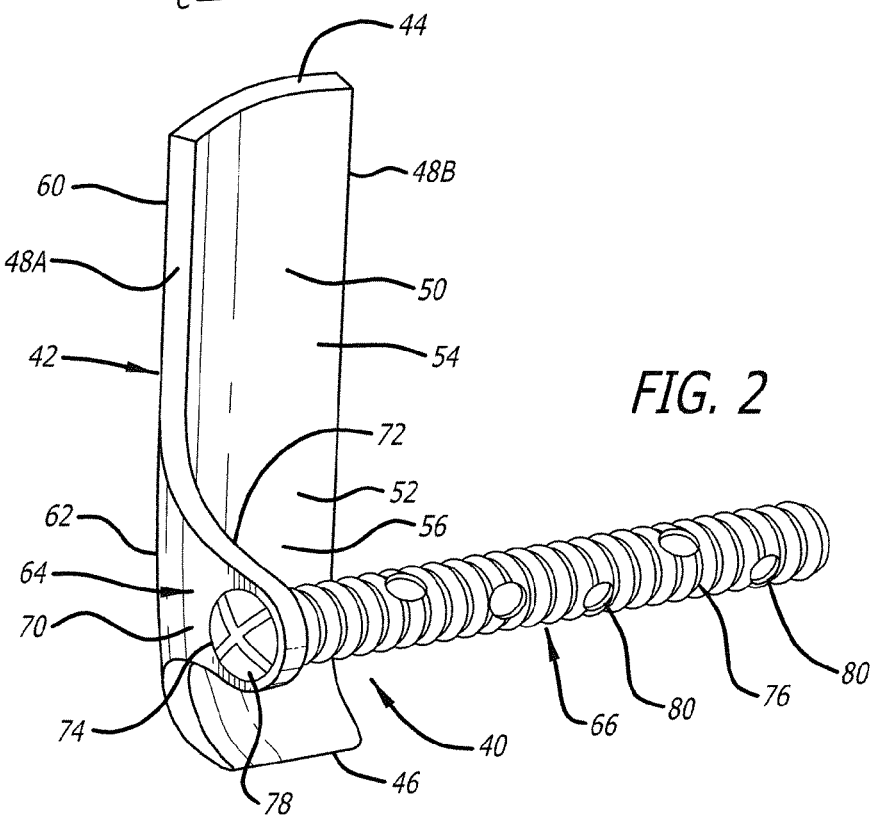

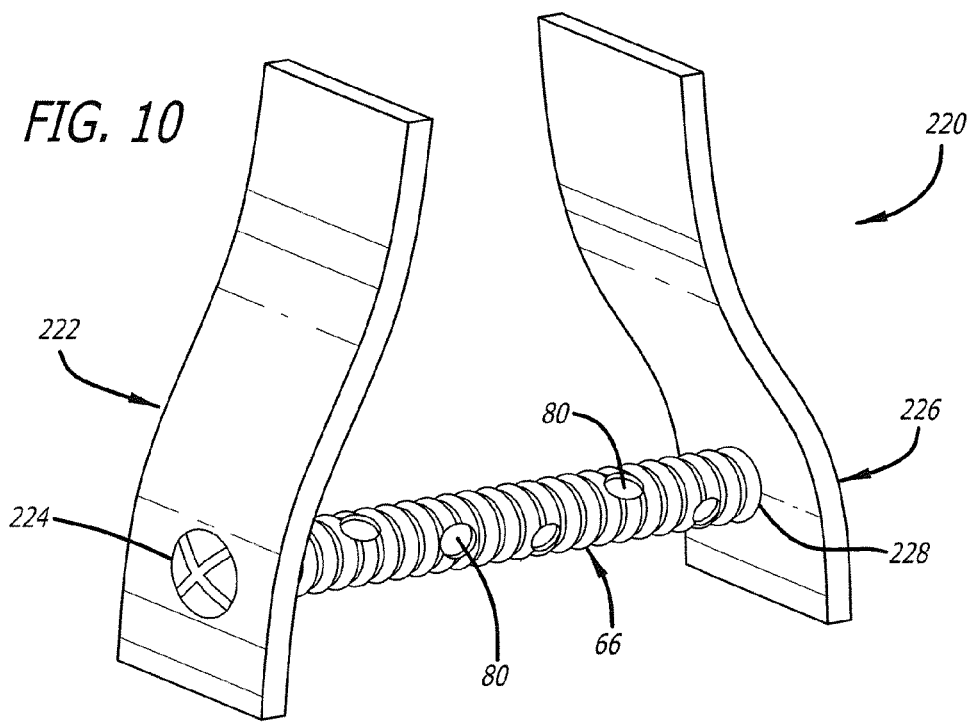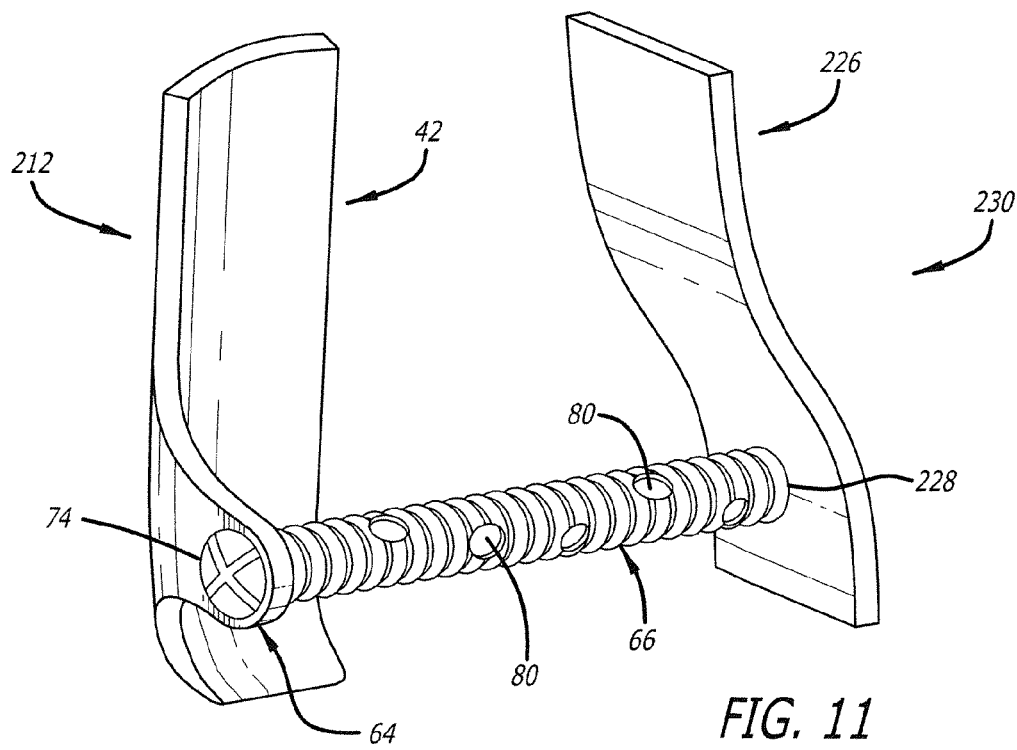

APPARATUS AND METHOD FOR USE OF THE APPARATUS FOR FRACTURE FIXATION OF THE DISTAL HUMERUS

The present application claims the benefit of Provisional Application No. 61/557,647, filed Nov. 9, 2011, the contents of which are incorporated herein by referenced.

BACKGROUND OF THE INVENTION

1. Field of the Invention

The present invention is generally related to a medical device and method for use thereof for facilitating repair of comminuted bone fractures. In particular, the present invention is related to an apparatus and method for use thereof to aid in the repair of comminuted bone fractures adjacent bone joints to restore joint viability. More specifically, the present invention relates to an apparatus and method for use thereof for repairing comminuted bone fractures adjacent bone joints by providing a fixation post to which bone fragments can be attached to afford healing of the comminuted bone fractures and facilitate restoration of movement associated with the bone joint.

2. Description of the Prior Art

Comminuted bone fractures adjacent joints oftentimes result in significant fragmentation of the bone. In fact, these types of bone fractures can often result in portions of the bone being severely fragmented, and the number of fragments created by these types of bone factures pose difficulties in repairing the bone. Bone plates have oftentimes been used to aid repair of the comminuted bone fractures. For example, when a trochlea and a capitellum (of a distal humerus) are severely fragmented during the injury process, a surgeon, even with the aid of conventional locking plates, may not be able to repair/restore the articular surface of such a fractured distal humerus. The potential for repair and restoration of the portions of the fractured distal humerus are limited, because the fractured portions thereof may be too small, fragmented, and/or fragile to accept a screw therethrough. As such, better boney fixation of bone fragments (such as the portions of the fractured distal humerus) is needed than that which can be achieved with conventional locking plates. Accordingly, there is a need for an apparatus in the form of a fracture fixation system and method for use of the apparatus for providing fracture fixation of comminuted bone fractures such as that of a fractured distal humerus.

SUMMARY OF THE INVENTION

The present invention in one preferred embodiment contemplates a system for fixing fractured bone portions of a distal humerus in position with respect to one another, the system including a plate portion including a first surface, an opposite second surface, a first end, a second end, and a length between the first and second ends, the second surface being adapted to contact a posterior portion of the distal humerus adjacent one of a lateral side and a medial side thereof; a projection portion extending outwardly from the second surface, the projection portion including a third surface, an opposite fourth surface, and an aperture therethrough between the third and fourth surfaces, the fourth surface being adapted to contact the one of the lateral and medial sides, and the aperture being adapted to receive a fixation post; the fixation post including a head portion, a shaft portion, a first end, an opposite second end, and a fenestration provided in the shaft portion, the shaft portion extending from the head portion to the second end, the head portion being adapted to engage the aperture formed in the projection portion, the shaft portion being adapted to engage the fractured bone portions and to extend from the one of lateral and medial sides to adjacent the other of the lateral and medial sides, and the fenestration being adapted to receive a cross member; and the cross member having a shaft portion, at least a portion of the shaft portion of the cross member being received in the fenestration to attach the fixation post and the cross member to one another, the cross member being adapted to engage the fractured bone portions adjacent the fixation post, where, when the fixation post is positioned with respect to the fractured bone portions, and the cross member is attached to the fixation post, the fixation post and the cross member serve in stabilizing the position of the fractured bone portions.

In another preferred embodiment, the present invention contemplates a system for fixing fractured bone portions of a distal humerus in position with respect to one another, the system including a first portion including a plate portion and a projection portion, the plate portion having a first surface, an opposite second surface, a first end, a second end, and a length between the first and second ends, the second surface being adapted to contact a posterior portion of the distal humerus adjacent one of a lateral side and a medial side thereof, the projection portion extending outwardly from the second surface, the projection portion having a third surface, an opposite fourth surface, and an aperture between the third and fourth surfaces, the fourth surface being adapted to contact the one of the lateral and medial sides, and the aperture of the projection portion being adapted to receive a fixation post; a second portion including a plate portion having a fifth surface, an opposite sixth surface, a first end, a second end, a length between the first and second ends, and an aperture between the fifth and sixth surfaces, the sixth surface being adapted to contact the other of the lateral and medial sides, and the aperture of the second portion being adapted to receive the fixation post; and the fixation post including a shaft portion, a first end, an opposite second end, and a fenestration provided in the shaft portion, the fixation post engaging the aperture of the first portion adjacent the first end thereof, the fixation post engaging the aperture of the second portion at the second end thereof, the shaft portion being adapted to engage the fractured bone portions and to extend between the lateral and medial sides of the distal humerus.

In yet another preferred embodiment, the present invention contemplates a system for fixing fractured bone portions of a distal humerus in position with respect to one another, the system including a plate portion including a first surface, an opposite second surface, an aperture therethrough between the first and second surfaces, a first end, a second end, and a length between the first and second ends, the second surface being adapted to contact a posterior portion of the distal humerus adjacent one of a lateral side and a medial side thereof; a first post adapted to be received in the aperture of the plate portion, the first post including a first end, an opposite second end, a shaft portion, and an aperture provided adjacent the second end of the first post, the first post engaging the aperture of the plate portion adjacent the first end thereof, the shaft portion adapted to extend outwardly from the second surface to engage the fractured bone portions adjacent the one of the lateral and medial sides, and the aperture of the first post being adapted to receive a second post; the second post including a head portion, a shaft portion, a first end, an opposite second end, and a fenestration provided in the shaft portion of the second post, and the shaft portion of the second post extending from the head portion to the second end of the second post, the head portion being adapted to engage the aperture provided in the first post, the shaft portion of the second post being adapted to engage the fractured bone portions and to extend from the one of lateral and medial sides to adjacent the other of the lateral and medial sides, and the fenestration being adapted to receive a cross member; and the cross member having a shaft portion, at least a portion of the shaft portion of the cross member being received in the fenestration to attach the second post and the cross member to one another, the cross member being adapted to engage the fractured bone portions adjacent the second post, where, when the first and second posts are positioned with respect to the fractured bone portions, and the cross member is attached to the second post, the first and second posts and the cross member serve in stabilizing the position of the fractured bone portions.

It is understood that both the foregoing general description and the following detailed description are exemplary and explanatory only, and are not restrictive of the invention as claimed.

BRIEF DESCRIPTION OF THE DRAWINGS

The accompanying drawings, which are incorporated in and constitute a part of the specification, illustrate preferred embodiments of the invention. Together with the description, they serve to explain the objects, advantages and principles of the invention. In the drawings:

FIG. 1 is a perspective view of a distal humerus cut off proximal to the joint line at the supracondylar level with prior art bone plates positioned with respect thereto;

FIG. 2 is a perspective view of a first illustrative embodiment of a fracture fixation system;

FIG. 10 is a perspective view of a fifth illustrative embodiment of the fracture fixation system incorporating a first plate and a second plate;

FIG. 11 is a perspective view of a sixth illustrative embodiment of the fracture fixation system incorporating a first plate similar to the plate portion depicted in FIGS. 2 and 3 in combination with a second plate similar to the second plate depicted in FIG. 10;

DETAILED DESCRIPTION OF THE PREFERRED EMBODIMENT

The fracture fixation systems of the present invention depicted in the accompanying drawings are used to facilitate repair and restoration of a fractured bone portion. In particular, the fracture fixation systems of the present invention can be used to repair and restore the articular surface of a fractured distal end of a humerus H. Thus, while the fracture fixations systems described below are discussed in association with the fractured distal end of humerus H, the fracture fixation systems can be used elsewhere in the body.

FIG. 1 depicts a lateral column LC and a medial column MC of a distal end of humerus H, and depicts various prior art bone plates 10, 12, 14, and 16. Bone plates 10 and 16 are applied medio-laterally, and bone plates 12 and 14 are applied posteriorly. Although all of bone plates 10, 12, 14, and 16 are depicted in FIG. 1, typically only one of bone plates 10, 12, 14, and 16 is applied relative to each of columns LC and MC. Nevertheless, surgeons can use one or more of bone plates 10, 12, 14, and 16 to stabilize comminuted bone portions of humerus H relative to the remainder thereof. However, even when using bone plates 10, 12, 14, and 16, difficulties remain in repairing and restoring comminuted portions of a trochlea T and a capitellum C when fractured.

As depicted in FIG. 1, bone plates 10, 12, 14, and 16 include apertures 20, 22, 24, and 26 for receiving bone screws (not shown) therethrough to facilitate attachment with comminuted bone portions and the remainder of humerus H. However, given that that the comminuted portions of trochlea T and capitellum C of humerus H may be too small, fragmented, and/or fragile to accept a screw therethrough, bone plates 10, 12, 14, and 16 are oftentimes unsuitable for repair and restoration of the distal end of humerus H. As discussed below, the fracture fixation systems of the present invention are provided to remedy the limitations of such prior art bone plates.

Figure 3:
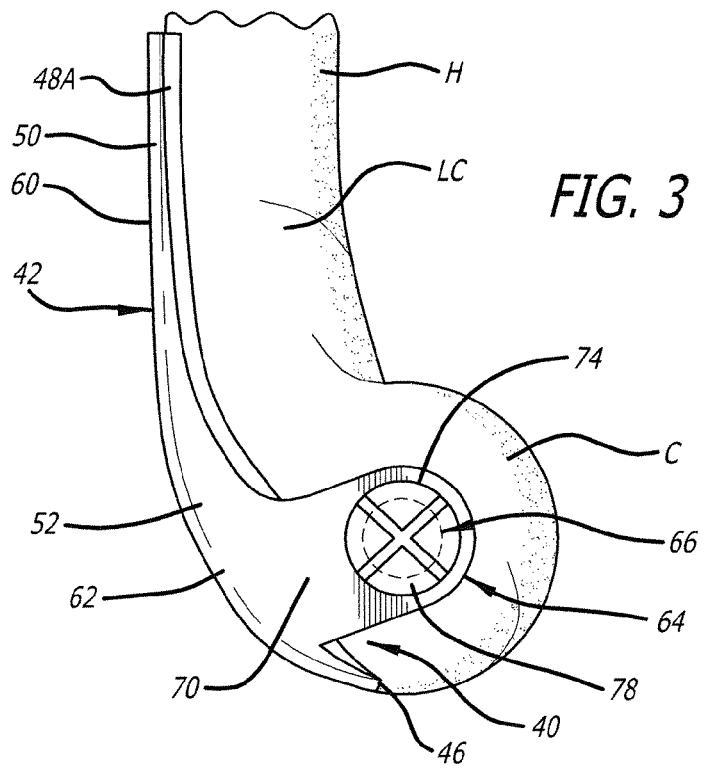
FIG. 3 is an elevational view of the first illustrative embodiment of the fracture fixation system positioned with respect to the lateral side of the distal humerus.

A first illustrative embodiment of the fracture fixation system is generally indicated by the numeral 40 in FIGS. 2 and 3. As depicted in FIGS. 2 and 3, fracture fixation system 40 includes a plate-shaped body 42, and, as discussed below, body 42 is configured to contact portions of humerus H to facilitate repair of comminuted portions of, for example, trochlea T and capitellum C.

Body 42 has a first end 44 and a second end 46 defining a length therebetween, and has a first side 48A and a second side 48B defining a width therebetween. Furthermore, body 42 can include apertures (not shown) for receiving bone screws or other fasteners (not shown) to facilitate attachment to humerus H, and includes a first plate portion 50 and a second plate portion 52. First plate portion 50 extends from first end 44 toward second end 46, and second plate portion 52 extends from second end 46 toward first end 44.

As depicted in FIGS. 2 and 3, first and second plate portions 50 and 52 are joined to one another adjacent the lengthwise center of body 42. Furthermore, while there is a smooth transition therebetween in FIGS. 2 and 3, the transition between first plate portion 50 and second plate portion 52 can be more abrupt.

First plate portion 50 includes a first bone-facing surface 54 that is slightly concave between first and second sides 48A and 48B. Second plate portion 52 includes a second bone-facing surface 56 that is slightly concave between first and second sides 48A and 48B and is concave from second end 46 toward first plate portion 50. As such, first and second bone-facing surfaces 54 and 56 are configured to contact portions of humerus H, and in doing so, can serve in cradling the comminuted portions thereof. For example, first and second bone-facing surfaces 54 and 56 can be configured to contact the posterior portions of distal end of the humerus H.

First and second plate portions 50 and 52 include first and second outer surfaces 60 and 62 opposite first and second bone-facing surfaces 54 and 56, respectively. Furthermore, first and second outer surfaces 60 and 62 can have shapes mirroring first and second bone-facing surfaces 54 and 56. The thickness of body 42 is defined between first and second bone-facing surfaces 54 and 56, and first and second outer surfaces 60 and 62, respectively. Moreover, given that there is a smooth transition between first and second plate portions 50 and 52, as depicted in FIGS. 2 and 3, first and second bone-facing surfaces 54 and 56 are smoothly transitioned into one another, and first and second outer surfaces 60 and 62 are smoothly transitioned into one another.

As discussed above, body 42 can be attached to humerus H. For example, one or more fasteners can be received through corresponding one or more apertures through first plate portion 50 and/or second plate portion 52. The one or more apertures can be provided between first and second bone-facing surfaces 54 and 56 and first and second outer surfaces 60 and 62, respectively, to receive the fasteners to secure body 42 to humerus H. Such fasteners can be used to attach body 42 to a posterior portion of humerus H.

The fracture fixation system 40 also can include one or more plate-shaped projections (or fins) 64 and one or more fixation posts 66. For example, as depicted in FIGS. 2 and 3, fracture fixation system 40 includes one projection 64 and one fixation post 66.

As depicted in FIGS. 2 and 3, projection 64 extends outwardly from first side 48A of body 42, and includes a first surface 70 (FIGS. 2 and 3) and a second (or bone-facing) surface 72 (FIG. 2). While projection 64 extends outwardly from first side 48A at a generally perpendicular angle with respect to second bone-facing surface 56, the angle of projection 64 is not limited thereto and can be varied with respect to directions defined by the length, the width, and the thickness of body 42. Second surface 72 can be configured to contact portions of the distal end of humerus H, and, together with bone-facing surfaces 54 and 56 serves in cradling the comminuted portions thereof.

Furthermore, as depicted in FIGS. 2 and 3, fixation post 66 is received through an aperture 74 formed between first and second surfaces 70 and 72 of projection 64. While fixation post 66 extends at a generally perpendicular angle with respect to projection 64 and is generally aligned with the width of body 42 in FIG. 3, the angle of fixation post 66 is not limited thereto. The angle of fixation post 66 can be varied with respect to projection 64, and thus, be varied with respect to the length, the width, and the thickness of body 42.

Fixation post 66 includes a shaft 76 and a head 78. Shaft 76 can have various lengths (FIGS. 9-11), and shaft 76 and head 78 can have different sizes and shapes (e.g., be configured to have cylindrical or frusto-conical shaped portions), and have regular roughened or rough surfaces (hereinafter regular roughened surfaces), irregular roughened or rough surfaces (hereinafter irregular roughened surfaces), and/or smoothened or smooth surfaces (hereinafter smoothened surfaces). The regular roughened surfaces are repeating patterns of surface protrusions or indentations (such as threads, ratchets, or similar structures), and the irregular roughened surfaces (such as barbs or similar structures) are non-repeating surface protrusions or indentations. For example, shafts 76 can be provided with threads and/or ratchets to facilitate attachment to the distal end of humerus H. Furthermore, by inserting fixation post 66 in aperture 74 and into the distal end of humerus H, fixation post 66 aids attachment of body 42 to humerus H. Moreover, if necessary, fixation post 66 can be locked to aperture 74 of projection 64. For example, this may be accomplished by providing complementary threads (not shown) on the exterior of head 78 and on the interior of aperture 74.

The fixation post 66 with or without fenestrations can be used to facilitate attachment of comminuted portions of the distal end of humerus H thereto. If no fenestrations are provided, sutures, wires, or cables can be wrapped around fixation post 66 to facilitate attachment of the comminuted portions of the distal end of the humerus H thereto.

If fenestrations are provided, one or more apertures 80 can extend transversely through shaft 76, and apertures 80 may be disposed in generally perpendicular relationship or at any desired angle with respect to longitudinal axis of shaft 76. Apertures 80, for example, can be disposed in generally perpendicular or transverse relationships with respect to each other. As discussed below, apertures 80 are used in anchoring comminuted portions of the distal end of humerus H with respect to the remainder of humerus H. For example, apertures 80 can be configured to receive cross members (such as cross members 200 depicted in FIG. 8) therethrough, and the cross members are used to secure the comminuted portions of the distal end of humerus H with respect to fracture fixation system 100 and the remainder of the humerus H.

Figure 4:
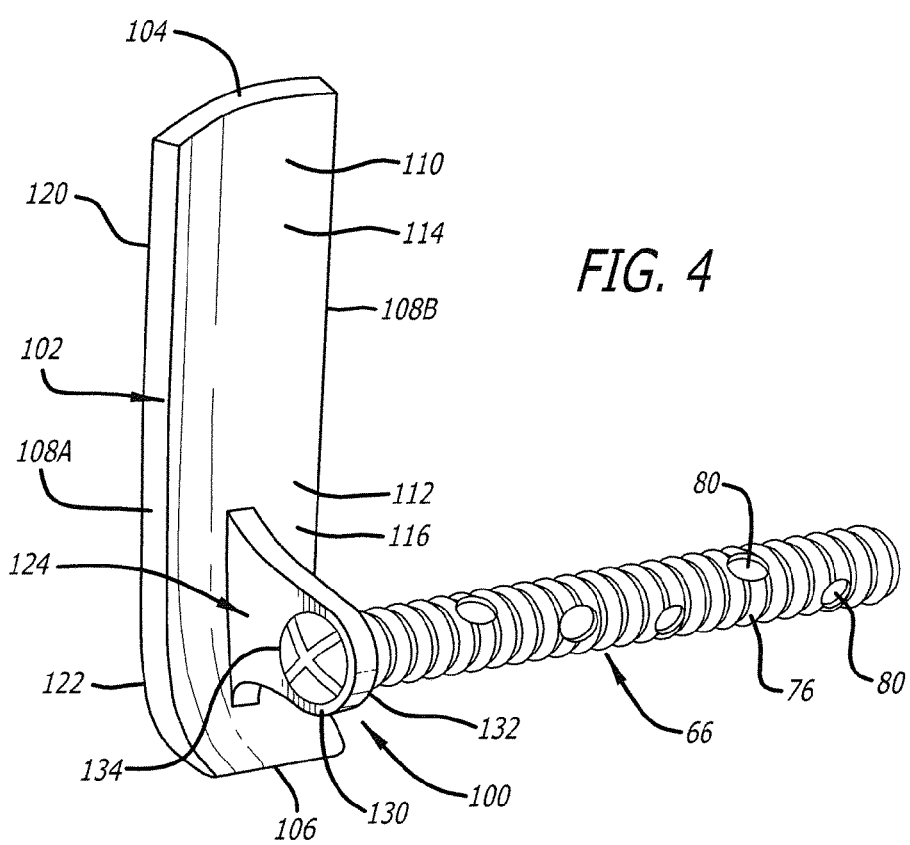
FIG. 4 is a perspective view of a second illustrative embodiment of the fracture fixation system.

A second illustrative embodiment of a fracture fixation system is generally indicated by numeral 100 in FIG. 4. Fracture fixation system 100 includes a plate-shaped body 102 that is configured to contact portions of humerus H. Body 102 has a first end 104 and a second end 106 defining a length therebetween, and has a first side 108A and a second side 108B defining a width therebetween. Body 102 can include apertures (not shown) for receiving bone screws or other fasteners (not shown) to facilitate attachment to humerus H, and includes a first plate portion 110 and a second plate portion 112 joined to one another adjacent the lengthwise center of body 102. First plate portion 110 extends from first end 104 toward second end 106, and second plate portion 112 extends from second end 106 toward first end 104. Furthermore, the joint between first and second plate portions 110 and 112 can be smooth (FIG. 4) or can be more abrupt.

First plate portion 110, as depicted in FIG. 4, includes a first bone-facing surface 114 that is slightly concave between first and second sides 108A and 108B. Furthermore, second plate portion 112, as depicted in FIG. 4, includes a second bone-facing surface 116 that is slightly concave between first and second sides 108A and 108B, and is concave from second end 106 toward first plate portion 110. First and second bone-facing surfaces 114 and 116 are configured to contact portions of humerus H, and, in doing so, can serve in cradling the comminuted portions thereof. For example, first and second bone-facing surfaces 114 and 116 can be configured to contact the posterior portions of the distal end of humerus H.

The first and second plate portions 110 and 112 include first and second outer surfaces 120 and 122, respectively. First and second outer surfaces 120 and 122 can have shapes mirroring first and second bone-facing surfaces 114 and 116. Furthermore, the thickness of body 102 is defined between first and second bone-facing surfaces 114 and 116, and first and second outer surfaces 120 and 122, respectively. Because there is a smooth transition between first and second plate portions 110 and 112, there are smooth transitions between first and second bone-facing surfaces 114 and 116, and between first and second outer surfaces 120 and 122.

As discussed above, body 102 can be attached to humerus H. For example, one or more fasteners can be received through corresponding one or more apertures through first plate portion 110 and/or second plate portion 112. The one or more apertures can be provided between first and second bone-facing surfaces 114 and 116 and first and second outer surfaces 120 and 122, respectively, to receive the fasteners to secure body 102 to humerus H. Such fasteners can be used to attach body 102 to a posterior portion of humerus H.

Fracture fixation system 100 also can include one or more plate-shaped projections (or fins) 124. Furthermore, fracture fixation system 100 can include one or more of fixation posts 66. For example, as depicted in FIG. 4, fracture fixation system 100 includes one projection 124 and one fixation post 66.

Figure 8:
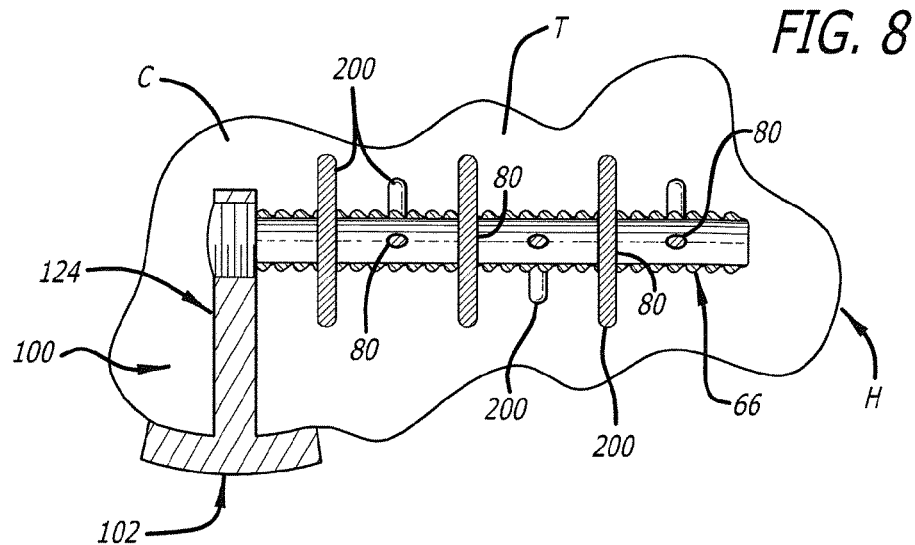
FIG. 8 is a partial cross-sectional view of the distal end of a humerus at the level of the joint with the second embodiment of the fracture fixation system positioned therein.

As depicted in FIG. 4, projection 124 extends outwardly from second bone-facing surface 116, and includes a first surface 130 and a second surface 132. As discussed below, both first and second surfaces 130 and 132 are configured to contact portions of distal end of humerus H (FIG. 8). As depicted in FIG. 4, projection 124 is positioned at the midpoint of the width of body 102. As such, given the position of projection 124 relative to body 102, projection 124 would ultimately be received in the interior of the distal end of the humerus H.

While projection 124 extends outwardly from second bone-facing surface 116 at a generally perpendicular angle with respect thereto, the angle of projection 124 is not limited thereto and can be varied with respect to directions defined by the length, the width, and the thickness of body 102. Furthermore, although projection 124 is positioned at the midpoint of the width of body 102, the position of projection 124 is not limited thereto—projection 124 can be positioned anywhere on bone facing surfaces 114 and 116 (of first and second plate portions 110 and 112). During use, projection 124 is buried within portions of the distal end of humerus H to avoid irritation of surrounding soft tissues such as ligaments and tendons.

As depicted in FIG. 4, fixation post 66 is received through an aperture 134 formed between first and second surfaces 130 and 132 of projection 124. As such, when fixation system 100 is positioned with respect to the distal end of humerus H, fixation post 66 and projection 124 would be received in the interior of distal end of humerus H. To that end, portions of the distal end of humerus H could be removed to facilitate receipt of fixation post 66 and projection 124. For example, a hole could be drilled through the distal end of the humerus H to facilitate receipt of fixation post 66.

When projection 124 is positioned with respect to humerus H, fixation post 66 would be inserted through a portion of the distal end of humerus H (between the exterior of humerus H and first surface 130), into aperture 134 and into a portion of the remainder of the distal end of humerus H. In doing so, fixation post 66 would aid attachment of body 102 to humerus H. Furthermore, in similar fashion to the relationship between fixation post 66 and projection 64 of fracture fixation system 40, fixation post 66 extends at a generally perpendicular angle with respect to projection 124 and is generally aligned with the width of body 102 in FIG. 4. However, the angle of fixation post 66 with respect to projection 124 is not limited thereto. The angle of fixation post 66 can be varied with respect to projection 124, and thus, can be varied with respect to the length, the width, and the thickness of body 102. Also, in similar fashion to the relationship between fixation post 66 and aperture 74 of projection 64, fixation post 66 can be locked to aperture 134 using complementary threads (not shown) on the exterior of head 78 (of fixation post 66) and on the interior of aperture 134. Additionally, head 78 can be elongated so that a portion thereof extends outwardly from first surface 130 of projection 124. As such, when fixation post 66 is received in aperture 134, a portion of a head 78 that is elongated could project or protrude from surface 130. Given the position of projection 124 relative to body 102, a head 78 that is elongated could fill a hole in the distal end of humerus through which fixation post 66 entered, so that a top surface of head 78 could be flush with the exterior of the distal end humerus H.

Rather than using projections 64 and 124 that are formed integrally with bodies 42 and 102, respectively, of fracture fixation systems 40 and 100, projections 64 and 124 can be formed separately from bodies 42 and 102 and thereafter be joined thereto. Regarding fracture fixation system 100, for example, a plate portion 140 including a projection (or fin) 142 and a base portion 144 (FIG. 5) can be provided. Plate portion 140 is formed separately from body 102, and thereafter is joined thereto.

Figure 5:
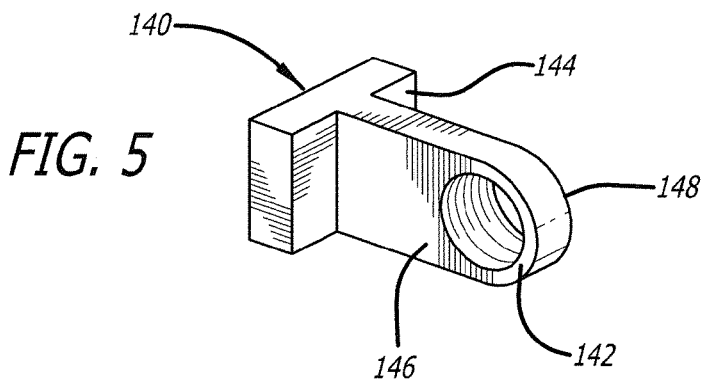
FIG. 5 is a perspective view of a fin element that can optionally be used with the second illustrative embodiment of the fracture fixation system.

As depicted in FIG. 5, projection 142 extends outward from base portion 144. Projection 142 is similar in function to projection 124, and includes a first surface 146 and a second surface 148. Projection 142 can be angled and positioned similarly to projection 124 with respect to body 102. Furthermore, base portion 144 can be used to attach plate portion 140 to body 102. For example, screws or other fasteners (not shown) can be received through base portion 144 and inserted into body 102 to attach plate portion 140 to body 102.

Figure 6:
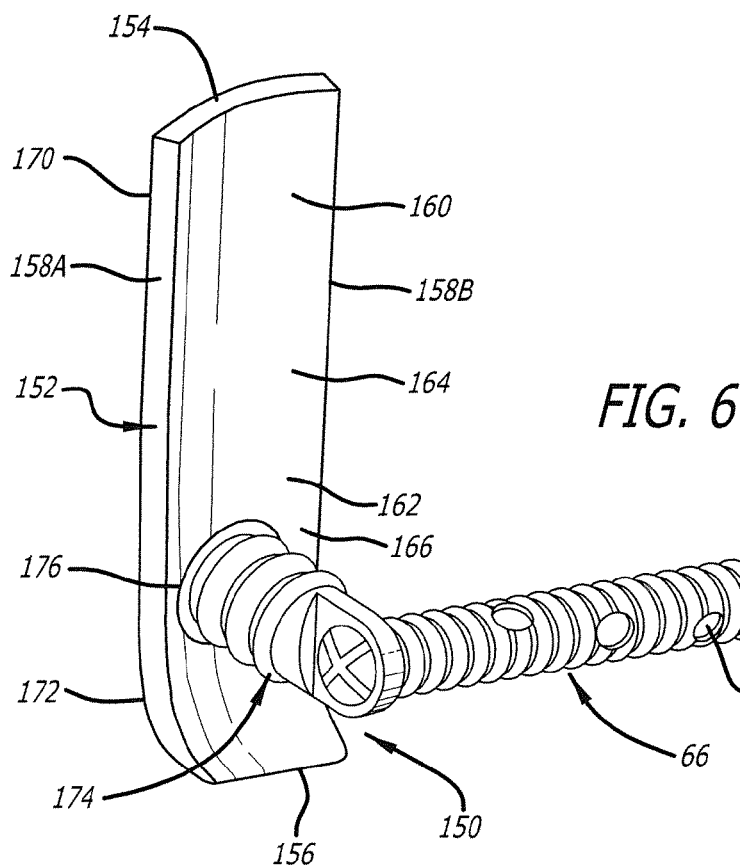
FIG. 6 is a perspective view of a third illustrative embodiment of the fracture fixation system.

A third illustrative embodiment of a fracture fixation system is generally indicated by the numeral 150 in FIG. 6. Fracture fixation system 150 includes a plate-shaped body 152 that is configured to contact portions of humerus H. The body 152 has a first end 154 and a second end 156 defining a length therebetween, and has a first side 158A and a second side 158B defining a width therebetween. Body 152 can include apertures (not shown) for receiving bone screws or other fasteners (not shown) to facilitate attachment to humerus H, and includes a first plate portion 160 and a second plate portion 162 joined to one another adjacent the lengthwise center of body 152. First plate portion 160 extends from first end 154 toward second end 156, and second plate portion 162 extends from second end 156 toward first end 154. Furthermore, the joint between first and second plate portions 160 and 162 can be smooth (FIG. 6) or can be more abrupt.

First plate portion 160, as depicted in FIG. 6, includes a first bone-facing surface 164 that is slightly concave between first and second sides 158A and 158B. Furthermore, second plate portion 162, as depicted in FIG. 6, includes a second bone-facing surface 166 that is slightly concave between first and second sides 158A and 158B, and is concave from second end 156 toward first plate portion 160. First and second bone-facing surfaces 164 and 166 are configured to contact portions of humerus H, and, in doing so, can serve in cradling the comminuted portions thereof. For example, first and second bone-facing surface 164 and 166 can be configured to contact the posterior portions of the distal end of humerus H.

First and second plate portions 160 and 162 include first and second outer surfaces 170 and 172, respectively. First and second outer surfaces 170 and 172 can have shapes mirroring first and second bone-facing surfaces 164 and 166. Furthermore, the thickness of body 152 is defined between first and second bone-facing surfaces 164 and 166, and first and second outer surfaces 170 and 172, respectively. Because there is a smooth transition between first and second plate portions 160 and 162, there are smooth transitions between first and second bone-facing surfaces 164 and 166, and between first and second outer surfaces 170 and 172.

As discussed above, body 152 can be attached to humerus H. For example, one or more fasteners can be received through corresponding one or more apertures through first plate portion 160 and/or second plate portion 162. The one or more apertures can be provided between first and second bone-facing surface 164 and 166 and first and second outer surfaces 170 and 172, respectively, to receive the fasteners to secure body 152 to humerus H. Such fasteners can be used to attach body 152 to a posterior portion of humerus H.

Figure 7:
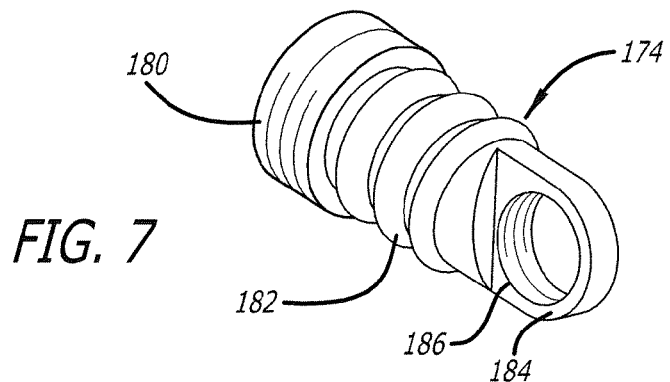
FIG. 7 is a perspective view of the fixation post depicted in FIG. 6.

Fracture fixation system 150 also can include one or more scaffold building posts 174 (FIGS. 6 and 7). Furthermore, fracture fixation system 150 can include one or more of fixation posts 66. For example, as depicted in FIG. 6, fracture fixation system 150 includes one scaffold building post 174 and one fixation post 66.

As depicted in FIG. 6, scaffold building post 174 is received through an aperture 176 formed in second plate portion 162, and portions thereof would ultimately be received in the interior of the distal end of humerus H. Aperture 176 extends between second bone-facing surface 166 and second outer surface 172. Furthermore, scaffold building post 174 can be different sizes and shapes (e.g., be configured to have cylindrical or frusto-conical shaped portions), and have the above-discussed regular roughened surfaces, irregular roughened surfaces, and/or smoothened surfaces. As such, scaffold building post 174 can include threaded or non-threaded portions, and, as depicted in FIG. 7, includes a head 180, a shaft 182, and end portion 184. As depicted in FIG. 7, for example, head 180 and shaft 182 are both threaded. Head 180 can be threaded to engage complementary threads (not shown) formed in aperture 176 to lock scaffold building post 174 to body 152. Furthermore, shaft 182 can be threaded to engage portions of the distal end of humerus H, and, in doing so, aid attachment of body 152 to humerus H.

As depicted in FIG. 6, aperture 176 (and hence, scaffold building post 174) is positioned at the midpoint of the width of body 152. While scaffold building post 174 extends outwardly from second bone-facing surface 166 at a generally perpendicular angle with respect thereto, the angle of scaffold building post 174 can be varied with respect to the directions defined by the length, the width, and thickness of body 152. Furthermore, although scaffold building post 174 is positioned at the midpoint of the width of body 152, the position of scaffold building post 174 is not limited thereto—aperture 176 (and hence, scaffold building post 174) can be positioned anywhere on first and second plate portions 160 and 162. During use, scaffold building post 174 (like projection 124) is inserted into portions of the distal end of humerus H to avoid irritation of surrounding soft tissues such as ligaments and tendons.

End portion 184 of scaffold building post 174 includes an aperture 186 for receiving fixation post 66. When fixation system 150 is positioned with respect to the distal end of humerus H, fixation post 66 and portions of scaffold building post 174 would be received in the interior of the distal end of humerus H. To that end, portions of the distal end of humerus H could be removed to facilitate receipt of fixation post 66 and portions of scaffold building post 174. For example, holes could be drilled through the distal end of humerus H to facilitate receipt of fixation post 66 and portions of scaffold building post 174.

When scaffold building post 174 is positioned with respect to humerus H, fixation post 66 would be inserted through a portion of the distal end of humerus H (between the exterior of humerus H and end portion 184), into aperture 186 and into a portion of the remainder of the distal end of humerus H. In doing so, fixation post 66 would aid attachment of body 152 to humerus H. Fixation post 66 extends at a generally perpendicular angle with respect to scaffold building post 174 and is generally aligned with the width of body 152 in FIG. 4. However, the angle of fixation post 66 with respect to scaffold building post 174 is not limited thereto. The angle of fixation post 66 can be varied with respect to scaffold building post 174, and thus, can be varied with respect to the length, the width, and the thickness of body 152. Furthermore, in similar fashion to the relationships between fixation post 66 and aperture 74 of projection 64 and between fixation post 66 and aperture 134 of projection 124, fixation post 66 can be locked to aperture 186 using complementary threads (not shown) on the exterior of head 78 (of fixation post 66) and on the interior of aperture 186. Additionally, as discussed above, head 78 can be elongated. As such, a head that is elongated could project or protrude from end portion 184 to potentially fill a hole in the distal end of humerus through which fixation post 66 entered, so that a top surface of head 78 could be flush with the exterior of the distal end of humerus H.

As discussed above, apertures 80 of fixation post 66 can be used to receive cross members (such as cross members 200 depicted in FIG. 8) therethrough. For example, after body 42 (of fracture fixation system 40) is attached to humerus H, bone-facing surfaces 54 and 56 (of first and second plate portions 50 and 52) and second surface 72 (of projection 64) are contacted to humerus H and the comminuted portions thereof, and fixation post 66 is inserted in aperture 74 and into the distal end of humerus H, cross members can be received in apertures 80 of fixation post 66 to aid in repair and restoration of the articular surface of the distal end of humerus H.

In addition, after body 102 (of fracture fixation system 100) is attached to humerus H, bone-facing surfaces 114 and 116 (of first and second plate portions 110 and 112) are contacted to humerus H and the comminuted portions thereof, projection 124 is buried within portions of the distal end of humerus H, and fixation post 66 is inserted into the distal end of humerus H and received in aperture 134, cross members can be received in apertures 80 of fixation post 66 to aid in repair and restoration of the articular surface of the distal end of humerus H.

Additionally, after body 152 (of fracture fixation system 150) is attached to humerus H, bone-facing surfaces 164 and 166 (of first and second plate portions 160 and 162) are contacted to humerus H and the comminuted portions thereof, scaffold building post 182 is inserted into portions of the distal end of humerus H, and fixation post 66 is inserted into the distal end of humerus H and received in aperture 186, cross members can be received in apertures 80 of fixation post 66 to aid in repair and restoration of the articular surface of the distal end of humerus H.

Figure 12A:
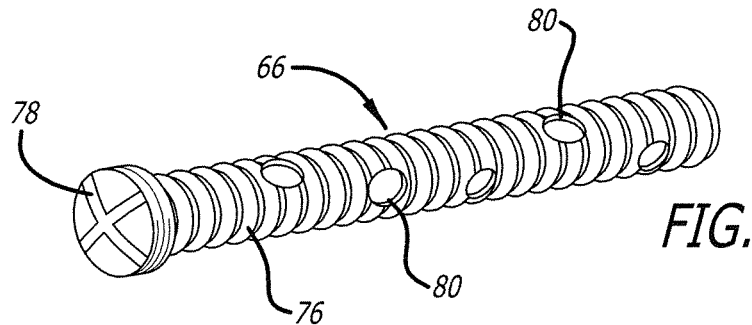
FIG. 12A is a perspective view of a first illustrative embodiment of a fixation post for use with the fracture fixation system.
Figure 12B:
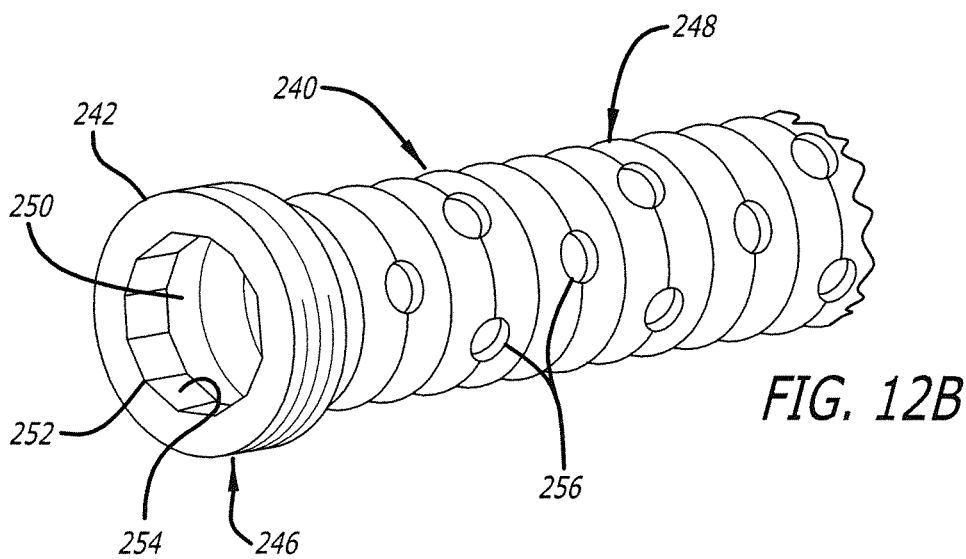
FIG. 12B is a fragmentary perspective view of a second illustrative embodiment of a fixation post for use with the fracture fixation system.

As depicted in FIG. 8, for example, fracture fixation system 100 is used in repairing and restoring the distal end of humerus H. As such, projection 124 is buried within portions of the distal end of humerus H, and fixation post 66 is inserted into the distal end of humerus H and received in aperture 134. Furthermore, as depicted in FIG. 8, cross members 200 are received in apertures 80 of fixation post 66 to afford support to portions of the distal end of humerus H. Cross members 200 can have configurations similar to fixation posts 66 (FIG. 12A), 240 (FIG. 12B), and 260 (FIG. 12B). Cross members 200 are disposed at various angles with respect to one another and to fixation post 66 according to the angles of apertures 80 formed in fixation post 66. As discussed above, apertures 80 can be disposed in generally perpendicular or transverse relationships with respect to one another and to fixation post 66.

Furthermore, cross members 200 can be different sizes and shapes (e.g., be configured to have cylindrical or frusto-conical shaped portions), and have the above-discussed regular roughened surfaces, irregular roughened surfaces, and/or smoothened surfaces. For example, cross members 200 can include threads (not shown) for engaging portions of humerus H and/or complementary threads formed in apertures 80.

Figure 9:
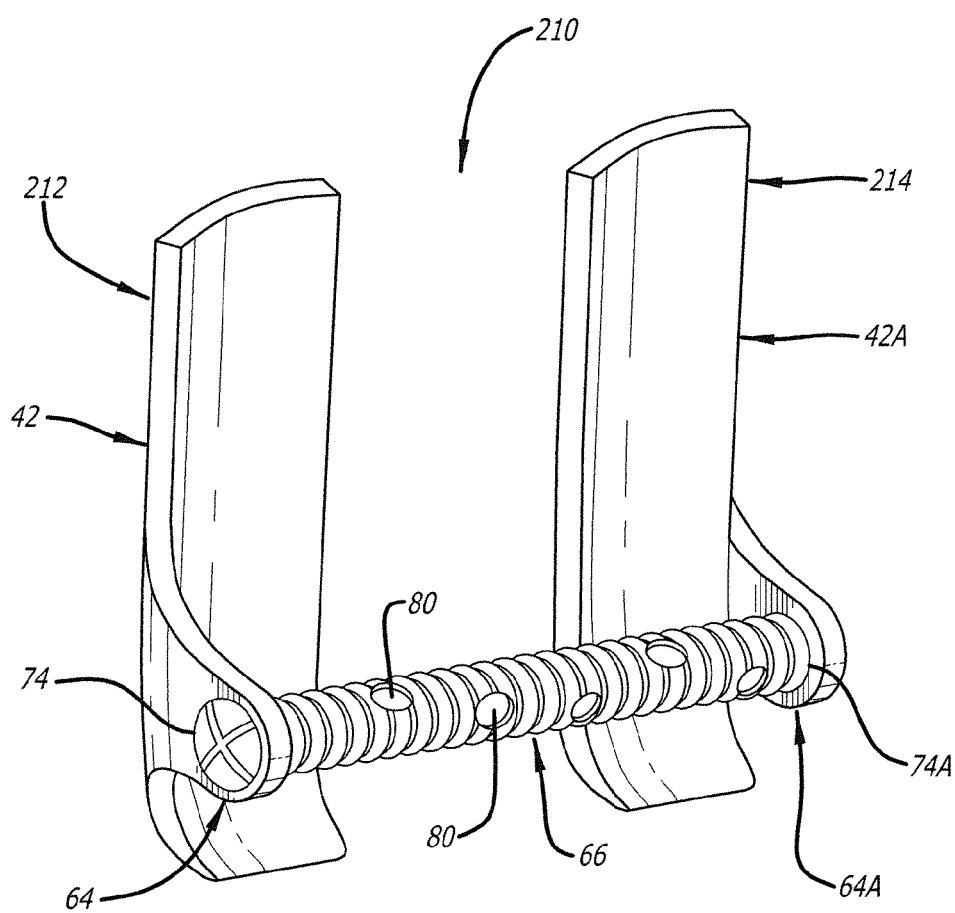
FIG. 9 is a perspective view of a fourth illustrative embodiment of the fracture fixation system incorporating a first plate portion similar to the plate portion depicted in FIGS. 2 and 3 in combination with a second plate portion similar to a mirror image of the plate portion depicted in FIGS. 2 and 3.

In addition to being used singularly, as depicted in FIGS. 9-11, more than one of fracture fixation systems 40, 100, and 150, modifications thereto, and/or components thereof can be used together. In particular, components of fracture fixation systems 40, 100, and 150 can be with used with modified components (such as oppositely configured analogues) thereof.

For example, as depicted in FIG. 9, a fourth illustrative embodiment of the fracture fixation system is generally indicated by the numeral 210. Fracture fixation system 210 includes a first portion referenced generally by the numeral 212 and a second portion referenced generally by the numeral 214. Fixation post 66 is shared between first and second portions 212 and 214.

First portion 212 can include body 42, projection 64, and aperture 74 formed through projection 64 of fracture fixation system 40. Furthermore, second portion 214 can be an analogue of first portion 212. That is, second portion 214 is similar to first portion 212, but is configured differently therefrom (e.g., oppositely configured) therefrom to contact different portions of the distal end of humerus H. For example, first portion 212 can be configured to contact posterior portions and a lateral first side portion of the distal end of humerus H, and second portion 214 can be configured to contact posterior portions and a medial second side portion of the distal end of humerus H. As such, second portion 214 includes a body 42A, a projection 64A, and an aperture 74A formed through projection 64A. First and second portions 212 and 214 can be attached to humerus H using one or more fasteners (not shown) received through corresponding one or more apertures (not shown) through first and second portions 212 and 214. For example, such fasteners can be used to attach first and second portions 212 and 214 to posterior portions of humerus H. Furthermore, first and second portions 212 and 214 are attached to one another using fixation post 66. Furthermore, fixation post 66 is received in apertures 74 and 74A, and although not shown, cross members can be received through apertures 80 of fixation post 66. If necessary fixation post 66 can include two heads to facilitate engagement with apertures 74 and 74A.

Furthermore, as depicted in FIG. 10, a fifth illustrative embodiment of the fracture fixation system is generally indicated by the numeral 220. Fracture fixation system 220 includes a first portion 222 shaped as a plate having a first aperture 224 and a second portion 226 shaped as a plate with a second aperture 228. First and second portions 222 and 226 are positioned on opposite sides (i.e. lateral and medial sides) of the distal end of humerus H and apertures 224 and 228 are configured to receive fixation post 66. First and second portions 222 and 226 can be attached to humerus H using one or more fasteners (not shown) received through corresponding one or more apertures (not shown) through first and second portions 222 and 226. For example, such fasteners can be used to attach first and second portions 222 and 226 to side portions of humerus H. Furthermore, as depicted in FIG. 10, first and second portions 222 and 226 are attached to one another using fixation post 66. As discussed above, fixation post 66 is received in apertures 224 and 228, and although not shown, cross members can be received through apertures 80 of fixation post 66. If necessary fixation post 66 can include two heads to facilitate engagement with apertures 224 and 228.

As depicted in FIG. 11, a sixth illustrative embodiment of the fracture fixation system is generally indicated by the numeral 230. Fracture fixation system 230 includes first portion 212 of fracture fixation system 210, and includes second portion 226 of fracture fixation system 220. As discussed above, first portion 212 includes aperture 74, and second portion 226 includes aperture 228. First portion 212 can be configured to contact posterior portions and a lateral first side portion of the distal end of humerus H, and second portion 226 can be configured to contact the opposite medial second side portion of the distal end of humerus H from first portion 212. First and second portions 212 and 226 can be attached to humerus H using one or more fasteners (not shown) received through corresponding one or more apertures (not shown) through first portion 212 and second portion 226. For example, such fasteners can be used to attach first portion 212 to posterior portions of humerus H, and to attach second portion 226 to side portions of humerus H. Furthermore, first portion 212 and second portion 226 are attached to one another using fixation post 66. Fixation post 66 is received in apertures 74 and 228, and although not shown, cross members can be received through apertures 80 of fixation post 66. If necessary fixation post 66 can include two heads to facilitate engagement with apertures 74 and 288.

As discussed above, fixation post 66 (FIG. 12A) includes shaft 76, head 78, and apertures (or fenestrations) 80 through shaft 76. Furthermore, shaft 76 can have various lengths, and can be provided with threads (as depicted in FIG. 12A) to facilitate attachment to the distal end of humerus H. Moreover, while shaft 76 and head 78 are substantially solid as depicted in FIG. 12A, shaft 76 can be hollow to serve as a cage to receive, for example, bone graft (not shown) therein.

For example, a first hollow fixation post is generally indicated by the numeral 240 in FIG. 12B. While first hollow fixation post 240 is depicted in FIG. 12B as having cylindrical portions, first hollow fixation post 240 can be different sizes and shapes (e.g., be configured to have cylindrical or frusto-conical shaped portions), and have the above-discussed regular roughened surfaces, irregular roughened surfaces, and/or smoothened surfaces. Furthermore, first hollow fixation post 240 includes a proximal end 242 and an opposite distal end (not shown). A head 246 is provided at proximal end 242, and a shaft 248 extends from head 246 to the distal end. First hollow fixation post 240 includes a hollow 250, and proximal end 242 thereof includes an opening 252 into hollow 250. The distal end can be open or closed to hollow 250, and head 246 and shaft 248 can include threads to facilitate engagement with a plate and/or bone. Head 246 can also include a tool engagement portion 254. First hollow fixation post 240 includes circular apertures (or fenestrations) 256 extending from the exterior of shaft 248 to hollow 250. While apertures 256 are circular, apertures 256 are not limited thereto. Apertures 256 can have different sizes and shapes. The apertures 256 can be configured to receive cross members or screws (not shown), and/or first hollow fixation post 240 can serve as a cage where bone growth can be facilitated through apertures 256 and into hollow 250.

Figure 12C:
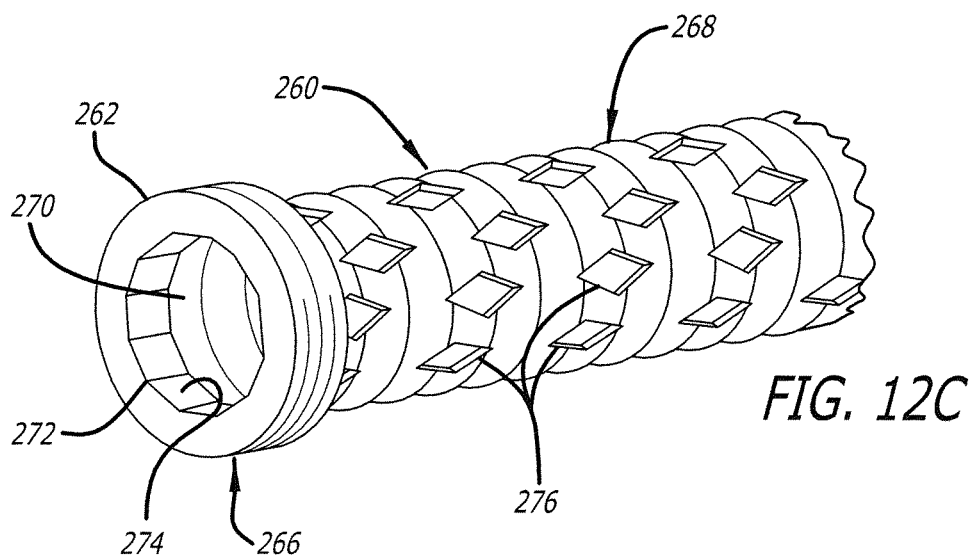
FIG. 12C is a fragmentary perspective view of a third illustrative embodiment of a fixation post for use with the fracture fixation system.

For example, a second hollow fixation post is generally indicated by the numeral 260 in FIG. 12C. While first hollow fixation post 260 is depicted in FIG. 12C as having cylindrical portions, first hollow fixation post 240 can be different sizes and shapes (e.g., be configured to have cylindrical or frusto-conical shaped portions), and have the above-discussed regular roughened surfaces, irregular roughened surfaces, and/or smoothened surfaces. Furthermore, second hollow fixation post 260 includes a proximal end 262 and an opposite distal end (not shown). A head 266 is provided at proximal end 262, and a shaft 268 extends from head 266 to the distal end. Second hollow fixation post 260 includes a hollow 270, and proximal end 262 thereof includes an opening 272 into hollow 270. The distal end can be open or closed to hollow 270, and head 266 and shaft 268 can include threads to facilitate engagement with a plate and/or bone. Head 266 can also include a tool engagement portion 274. Second hollow fixation post 260 includes quadrilateral apertures (or fenestrations) 276 extending from the exterior of shaft 268 to hollow 270. While apertures 276 are quadrilateral, apertures 276 are not limited thereto. Apertures 276 can have different sizes and shapes. The apertures 276 can be configured to receive cross members or screws (not shown), and/or second hollow fixation post 260 can serve as a cage where bone growth can be facilitated through apertures 276 and into hollow 270.

Other embodiments of the invention will be apparent to those skilled in the art from consideration of the specification and practice of the invention disclosed herein. Accordingly, it is intended that the specification and examples be considered as exemplary only.

I claim:

1. A system for fixing fractured bone portions of a distal humerus in position with respect to one another, the system comprising:

a plate portion including a first surface, an opposite second surface, a first end, a second end, and a length between the first and second ends, the second surface being configured to contact a posterior portion of the distal humerus adjacent one of a lateral side and a medial side thereof;

a projection portion extending outwardly from the second surface, the projection portion including a third surface, an opposite fourth surface, and an aperture therethrough between the third and fourth surfaces, the fourth surface being configured to contact the one of the lateral and medial sides, and the aperture being configured to receive a fixation post;

the fixation post including a head portion, a shaft portion, a first end, an opposite second end, and plurality of fenestrations provided in the shaft portion, the shaft portion extending from the head portion to the second end, the head portion being configured to engage the aperture formed in the projection portion, the shaft portion being configured to engage the fractured bone portions and to extend from the one of lateral and medial sides to adjacent the other of the lateral and medial sides, each of the fenestrations having a longitudinal axis, wherein the longitudinal axes are not parallel to each other, and each of the fenestrations being configured to receive a cross member; and each of the cross members having a shaft portion, at least a portion of the shaft portion of each of the cross members being received in one of the fenestrations to attach the fixation post to each of the cross members, each of the cross members being configured to engage the fractured bone portions adjacent the fixation post, wherein, when the fixation post is positioned with respect to the fractured bone portions, and each of the cross members is attached to the fixation post, the fixation post and the cross members serve in stabilizing the position of the fractured bone portions.

2. The system of claim 1, wherein the fixation post is one of threaded and ratcheted to facilitate engagement with the fractured bone portions.

3. The system of claim 1, wherein each of the cross members is threaded to facilitate complementary engagement with threads provided in the corresponding fenestration.

4. The system of claim 1, wherein the plate portion includes an aperture configured to receive a fastener therethrough for attaching the plate portion to the distal humerus.

5. The system of claim 1, wherein the plate portion includes a first edge and a second edge formed on opposites sides of the plate portion between the first and second ends, the projection portion extending outwardly from the second surface between the first and second edges.

6. The system of claim 1, wherein the fixation post is at least partially hollow.

7. A system for fixing fractured bone portions of a distal humerus in position with respect to one another, the system comprising:

a plate portion including a first surface, an opposite second surface, an aperture therethrough between the first and second surfaces, a first end, a second end, and a length between the first and second ends, the second surface being configured to contact a posterior portion of the distal humerus adjacent one of a lateral side and a medial side thereof;

a first post configured to be received in the aperture of the plate portion, the first post including a first end, an opposite second end, a shaft portion, and an aperture provided adjacent the second end of the first post, the first post engaging the aperture of the plate portion adjacent the first end thereof, the shaft portion configured to extend outwardly from the second surface to engage the fractured bone portions adjacent the one of the lateral and medial sides, and the aperture of the first post being configured to receive a second post;

the second post including a head portion, a shaft portion, a first end, an opposite second end, and a fenestration provided in the shaft portion of the second post, and the shaft portion of the second post extending from the head portion to the second end of the second post, the head portion being configured to engage the aperture provided in the first post, the shaft portion of the second post being configured to engage the fractured bone portions and to extend from the one of the lateral and medial sides to adjacent the other of the lateral and medial sides, and the fenestration being configured to receive a cross member; and the cross member having a shaft portion, at least a portion of the shaft portion of the cross member being received in the fenestration to attach the second post and the cross member to one another, the cross member being configured to engage the fractured bone portions adjacent the second post, wherein, when the first and second posts are positioned with respect to the fractured bone portions, and the cross member is attached to the second post, the first and second posts and the cross member serve in stabilizing the position of the fractured bone portions.

8. The system of claim 7, wherein the first and second posts are one of threaded and ratcheted to facilitate engagement with the fractured bone portions.

9. The system of claim 7, wherein the plate portion includes an aperture configured to receive a fastener therethrough for attaching the plate portion to the distal humerus.

* * * * *